US00PP26405P3

(12) United States Plant Patent
Clark et al.

(10) Patent No.: US PP26,405 P3
(45) Date of Patent: Feb. 9, 2016

(54) BLACKBERRY PLANT NAMED 'A-1960'

(50) Latin Name: ***Rubus* subgenus *Rubus* Watson**
Varietal Denomination: A-1960

(71) Applicant: THE BOARD OF TRUSTEES OF THE UNIVERSITY OF ARKANSAS, Little Rock, AR (US)

(72) Inventors: John Reuben Clark, Fayetteville, AR (US); James N. Moore, Arlington, TX (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 189 days.

(21) Appl. No.: 13/998,724

(22) Filed: Nov. 27, 2013

(65) Prior Publication Data

US 2015/0150169 P1 May 28, 2015

(51) Int. Cl.
*A01H 5/08* (2006.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |
| PP24,249 | P3 | 2/2014 | Clark |

OTHER PUBLICATIONS

Ruple, A. et al., "An evaluation of fertility in Arkansas primocane-fruiting blackberries," (2010) Hort. Science 45:1-6.
U.S. Appl. No. 13/987,214, filed Jul. 11, 2013.
Website for Heaven Can Wait Blackberry, http://www.gurneys.com/product/heaven_can_wait_blackberry, downloaded Oct. 15, 2014.

*Primary Examiner* — Susan McCormick Ewoldt
(74) *Attorney, Agent, or Firm* — Andrus Intellectual Property Law, LLP

(57) ABSTRACT

Description and specifications of a new and distinct blackberry cultivar named 'A-1960' which originated from seed produced by a hand pollinated cross of Ark. Selection Ark.-1583 (non-patented, unreleased genotype; female)×Ark.-1482 (non-patented, unreleased genotype; male) is provided. This new blackberry cultivar can be distinguished by its very firm fruit with long shape, medium-large size, attractive fruit appearance, very good flavor, excellent plant health, and cane erectness.

2 Drawing Sheets

Latin name: *Rubus* subgenus *Rubus* Watson.

BACKGROUND

The new floricane-fruiting cultivar of blackberry called 'A-1960' is described herein. The new cultivar originated from a hand-pollinated cross of Ark. selections Ark.-1583× Ark.-1482 made in 1991. The seeds resulting from this controlled hybridization were germinated in a greenhouse in the spring of 1992 and planted in a field near Clarksville, Ark. (West-Central Arkansas). The seedlings fruited in the summer of 1994. One seedling, designated 'A-1960', was selected in 1994 for its very firm fruit with long shape, medium-large size, attractive fruit appearance, very good flavor, excellent plant health, and cane erectness.

SUMMARY OF THE INVENTION

The new and distinct cultivar of blackberry originated from a hand-pollinated cross of Ark. Selection Ark.-1583 (non-patented, unreleased genotype; female)×Ark.-1482 (non-patented, unreleased genotype; male) made in 1991 and located near Clarksville, Ark. (West-Central Arkansas). The botanical designation of the new cultivar of blackberry is *Rubus* subgenus *Rubus* Watson.

The seeds resulting from this controlled hybridization were germinated in a greenhouse in the spring of 1992 and planted in a field near Clarksville, Ark. The seedlings fruited in the summer of 1994 on floricanes. One seedling, designated 'A-1960', was selected in 1994 for its very firm fruit with long shape, medium-large size, attractive fruit appearance, very good flavor, excellent plant health, and cane erectness.

During 1994, the original plant selection was propagated asexually from root cuttings at the above-noted location, and a test row of 10 plants was established. Subsequently, larger test plantings have been established with asexually multiplied plants at two locations in Arkansas. At each location propagation was from root cuttings from the Clarksville, Ark. test plot.

The new cultivar has been asexually multiplied since 1994 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety, in a plant that is 16 years of age, in color as nearly true as it is reasonably possible to make in a color illustration of this character.

DETAILED DESCRIPTION OF THE NEW CULTIVAR 'A-1960'

Figure 1:
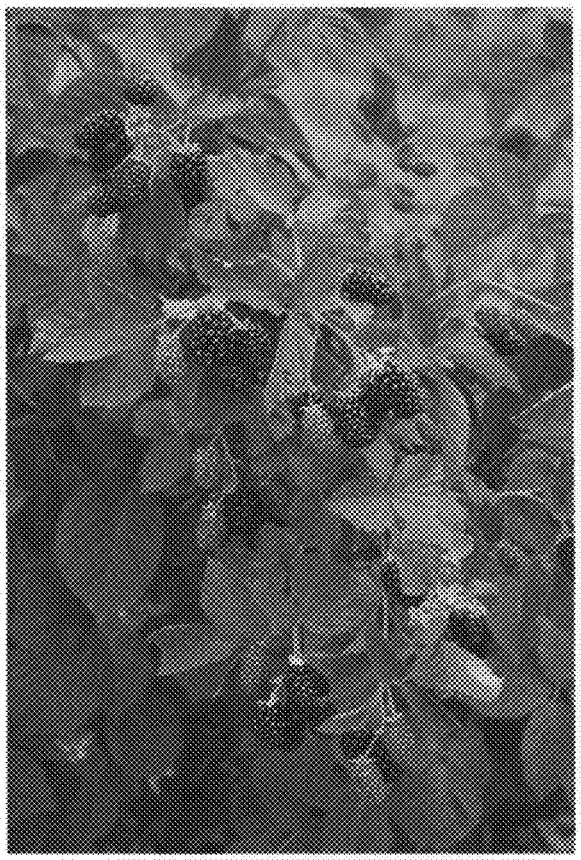
FIG. 1 is a photograph of blackberry canes of 'A-1960' taken near Clarksville, Ark.
Figure 2:
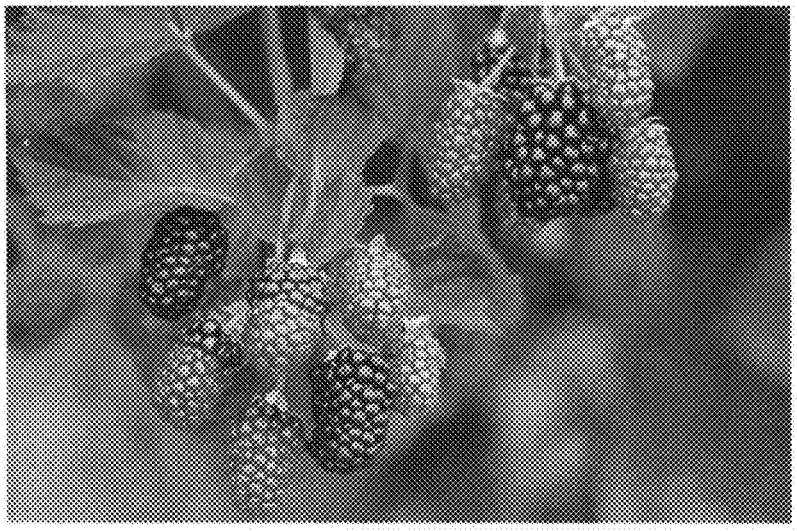
FIG. 2 is a photograph of ripe and unripe fruit on the plant of 'A-1960'.
Figure 3:
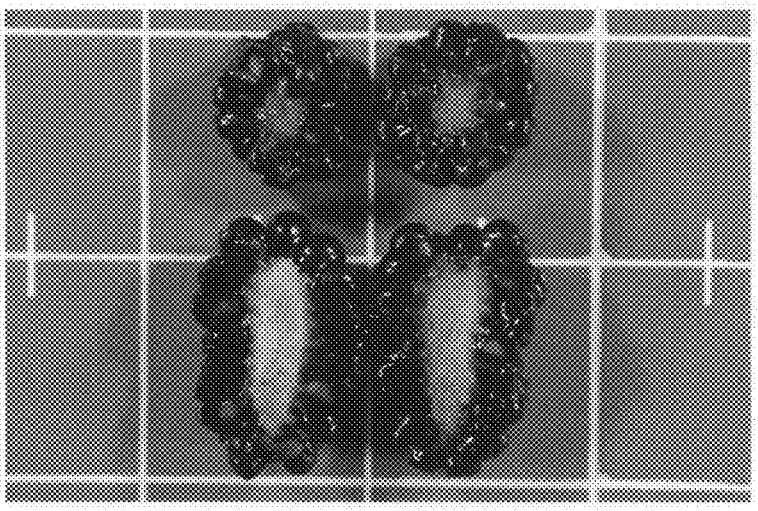
FIG. 3 is a photograph of ripe fruit of 'A-1960' cut horizontally and longitudinally.
Figure 4:
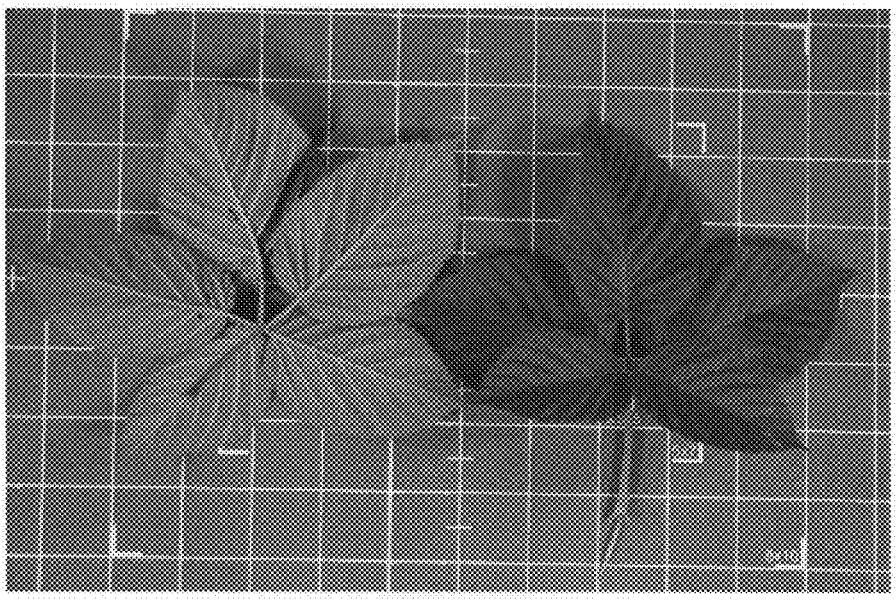
FIG. 4 is a photograph showing the abaxial (left) and adaxial (right) sides of a primocane leaf of 'A-1960'.

Plants and fruit of this new cultivar differ phenotypically from its parents. The new cultivar is later ripening and sweeter than parent 'A-1583', and later ripening, more even drupelet set and is larger than parent 'A-1482'. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit are moderately resistant to anthracnose [*Elsinoe veneta* (Burkh.) Jenkins], and plants appear immune to orange rust [*Gymnoconia nitens* (Schwein.) F. Kern and H. W. Thurston.]. No screening has been done for resistance to double blossom/rosette [*Cercosporella rubi* (Wint.) Plakidas]

The bloom period of the new cultivar begins on average 23 April for 10% bloom and 27 April for 50% bloom. This is two days earlier than for Apache (U.S. Plant Pat. No. 11,865) and the same as Ouachita (U.S. Plant Pat. No. 17,162).

Floricane fruit of the new cultivar begins ripening 4 days before Ouachita and about 7 days before Apache and ends about the same time as Ouachita. Average first ripening date is 6 June in West-Central Arkansas. The average floricane fruiting period is 40-50 days.

Fruit yields of the new cultivar on floricanes are usually 1.5 to 2.0 kg (3 to 4.5 lb/plant), comparable to Ouachita, in West-Central Arkansas.

The fruit is elongated to slightly conical in shape, black in color, and very attractive. The floricane fruit is medium-large (5-6 g) similar to Ouachita. Fruit size of the new cultivar is maintained well throughout the entire harvest season.

The fresh fruit rates very well in flavor, comparable to Ouachita and Apache. The soluble solids concentration averages about 11-12% on shiny black fruit comparable to Apache and Ouachita. Fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were 16 years old and grown on a fine sandy loam soil with sprinkler irrigation near Clarksville, Ark. The plants were fertilized near budbreak (late March on average) with complete or nitrogen fertilizer, and had an additional nitrogen fertilizer application in early July. Primocanes were tipped at approximately 45 inches, and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size*.—Plants are grown in a hedgerow and primocanes tipped at approximately 45 inches; plants in this system then range in size from about 45 to 55 inches tall and approximately 24-36 inches wide at the top.

*Growth habit*.—Moderate vigor, canes erect; suckers from crown and roots.

*Growth rate*.—First emergence of primocanes is 24 March and primocanes reach tipping height (107 cm) on 31 May.

*Productivity*.—Floricane — between 1.5 and 2 kg (slightly over 4.45 lb/plant), comparable to Ouachita.

*Cold hardiness*.—Hardy to 8° (−13° C.) or lower comparable Ouachita.

*Canes*.—Thornless, erect. Floricane (dormant or winter cane): Cane diameter: base 1.40 cm; midpoint 1.11 cm; terminal 0.55 cm. Internode length: base 9.31 cm; midpoint 5.14 cm; terminal 1.63 cm. Floricane color: base Greyed Orange Group (166A); midpoint Greyed-Purple Group (185A) over Green Group (137B); terminus Greyed-Purple Group (185A) over Green Group (137C). Primocane (current-season cane): Cane diameter: base 1.65 cm; midpoint 1.20 cm; terminal 0.88 cm. Internode length: base 4.34 cm; midpoint 6.10 cm; terminal 3.11 cm. Primocane color: base Red Group (46A) over Green Group (139B); midpoint Red Group (46A) over Green Group (141C); terminus Red Group (46A) over Yellow-Green Group (146B). Date of primocane emergence: 24 March.

*Disease resistance*.—Moderate resistance to anthracnose, and plants appear immune to orange rust. No screening has been done for resistance to double blossom/rosette.

Foliage:

*Primocane*.—Leaves: medium; mature compound leaf width 16.06 cm; length 11.18 cm. Leaflet: Width 6.36 cm; length 8.98 cm; shape round to slightly elongated with acuminate apex and round, slightly flat base; margin doubly serrated, serration teeth length 0.16 cm and width 0.24 cm; pubescence is very light on abaxial and adaxial surfaces; number of leaflets per compound leaf 5. Color: Base abaxial Yellow-Green Group (146A); adaxial Green Group (139A); midpoint abaxial Yellow-Green Group (146A); adaxial Green Group (139A); terminal abaxial Yellow-Green Group (146C); adaxial Green Group (137A). Venation Pattern: pinnate. Vein Color: (mature primocane leaf) abaxial: yellow green group 143-D, (mature primocane leaf) adaxial: green group 137-C, (young primocane leaf) abaxial: yellow green group 147-B, (young primocane leaf) adaxial: yellow green group 147-B. Petioles: Length: 6.12 cm; color: Red Purple Group (60A) over Yellow Green Group (144A); texture: smooth. Petiolules: Length: 1.38 cm; color: Red Purple Group (60A) over Yellow Green Group (144A); texture: smooth. Stipules: Length: 0.83 cm; width: 0.06 cm; color: Green Group (137C); texture: smooth.

*Floricane*.—Leaves: Medium; mature compound leaf width 11.74 cm; length 8.73 cm. Leaflet: Width 6.43 cm; length 7.00 cm; shape round, slightly elongated with acuminate apex and rounded base; margin double serrated, with serration teeth length 0.25 cm and width at base 0.34 cm; pubescence is lightly present on abaxial and adaxial sides. Number of leaflets per compound leaf is 3 most commonly but occasionally up to 5. Color: base abaxial Green Group (130A); adaxial Green Group (135A); midpoint abaxial Green Group (137C); adaxial Green Group (132A); terminal abaxial Green Group (137A); adaxial Green Group (139A). Petioles: Length 5.20 cm; color: Green Group (139B) texture: smooth. Petiolules: Length 0.40 cm; color: Green Group (139B); texture: smooth. Stipules: Length 0.63 cm; width: 0.13 cm; color: Green Group (137C); texture: smooth.

Flowers:

*Floricane*.—Date of bloom: 23 April for 10% bloom and 27 April for 50% bloom; two days earlier than for Apache and the same as Ouachita. Petal color: White Group 155-C on both the upper and lower surfaces. Reproductive organs: Stamens — erect, numerous. Pistils — numerous. Pollen — normal, fertile, and abundant. Flower diameter: 3.6 cm. Petal size: Length 1.6 cm; width 1.3 cm. Average number flowers per cluster: 3. Average number of petals per flower: 7. Number of sepals per flower: 5. Peduncle length: 1.1 cm. Peduncle color: Yellow-Green Group (144A). Cyme type: Elongate simple cyme.

Fruit:

*Floricane*.—Maturity — average first ripe 4 days before Ouachita and about 7 days before Apache and ends about the same time as Ouachita. Average first ripening date is 6 June in West-Central Arkansas. The average floricane fruiting period is 40-50 days. Size: medium-large, average 5-6 g. Diameter of fruit at primary position on inflorescence: equator 2.03 cm; base pole 1.41 cm; terminal pole 1.22 cm. Diameter of fruit at secondary positions on inflorescence: equator 1.86 cm; base pole 1.46 cm; terminal pole 1.09 cm. Length (primary fruit): 2.68 cm. Shape: elongated to slightly conical. Color: Black Group (202A). Drupelet size: 0.47 cm. Seed: average length 3.94 mm, width 2.10 mm; dry weight 4.11 mg. Soluble solids: 11-12%. pH: 3.19. Acidity: 1.46 g/100 ml expressed as citric acid. Processed quality: Not evaluated for processing. Uses: home garden and fresh market use are primary intended uses due to posttharvest handling potential is not as good as many other thornless cultivars developed for the shipping market.

The cultivar: The most distinctive features of the cultivar are very firm fruit with long shape, medium-large size, attractive fruit appearance, very good flavor, excellent plant health, and cane erectness.

We claim:

1. A new and distinct cultivar of blackberry plant named 'A-1960,' substantially as illustrated and described herein.

* * * * *